(12) United States Patent
Haslbeck

(10) Patent No.: US 10,646,647 B2
(45) Date of Patent: May 12, 2020

(54) ADJUSTING DEVICE FOR A FLOW CONTROLLER

(71) Applicant: B. Braun Melsungen AG, Melsungen (DE)

(72) Inventor: Karsten Haslbeck, Melsungen (DE)

(73) Assignee: B. Braun Melsungen AG (DE)

(*) Notice: Subject to any disclaimer, the term of this patent is extended or adjusted under 35 U.S.C. 154(b) by 145 days.

(21) Appl. No.: 14/899,372

(22) PCT Filed: Jun. 24, 2014

(86) PCT No.: PCT/EP2014/063312
§ 371 (c)(1),
(2) Date: Dec. 17, 2015

(87) PCT Pub. No.: WO2014/206998
PCT Pub. Date: Dec. 31, 2014

(65) Prior Publication Data
US 2016/0144112 A1    May 26, 2016

(30) Foreign Application Priority Data

Jun. 26, 2013 (DE) .......................... 10 2013 212 325

(51) Int. Cl.
*A61M 5/168* (2006.01)
*F16K 31/60* (2006.01)
(Continued)

(52) U.S. Cl.
CPC .... *A61M 5/16881* (2013.01); *A61M 5/16877* (2013.01); *A61M 5/3155* (2013.01);
(Continued)

(58) Field of Classification Search
CPC .......... A61M 5/16881; A61M 5/16813; A61M 5/16877; A61M 15/002; A61M 5/16804;
(Continued)

(56) References Cited

U.S. PATENT DOCUMENTS 3,399,676 A * 9/1968 McLaughlin ......... A61M 3/025
137/268
3,499,127 A    3/1970 Cherry et al.
(Continued)

FOREIGN PATENT DOCUMENTS

DE    7811534 U1    2/1979
DE    3590339 C2    3/1992
(Continued)

OTHER PUBLICATIONS

European Patent Office International Search Report for Corresponding International Application No. PCT/EP2014/063312, dated Sep. 3, 2014 in the English and German Languages (8 pgs).
(Continued)

*Primary Examiner* — Nathan R Price
*Assistant Examiner* — Justin L Zamory
(74) *Attorney, Agent, or Firm* — RatnerPrestia

(57) ABSTRACT

An adjusting device for adjusting the flow rate of a medicinal fluid-conveying system, said device having a selection wheel for selecting one of a number of possible flow rates, having an adjusting disc connected to said selection wheel for adjusting the selected flow rate, and having a catching nose that cooperates with the outer edge of the adjusting disc, is improved in that the adjusting disc has a star shape.

13 Claims, 2 Drawing Sheets

(51) Int. Cl.
  *A61M 39/28* (2006.01)
  *A61M 5/315* (2006.01)
  *F16K 35/04* (2006.01)

(52) U.S. Cl.
  CPC ........ *A61M 5/3156* (2013.01); *A61M 39/286* (2013.01); *F16K 31/60* (2013.01); *F16K 35/04* (2013.01); *A61M 2205/3334* (2013.01)

(58) Field of Classification Search
  CPC ..... A61M 39/22; H01H 19/001; H01H 19/14; H01H 19/46; H01H 19/48; H01H 19/56; H01H 19/58; G01D 5/04; G01D 5/1655; G01D 5/24433
  USPC ....... 604/8, 9, 118, 207, 246, 247, 254, 256, 604/890.1
  See application file for complete search history.

(56) References Cited

U.S. PATENT DOCUMENTS

| | | | |
|---|---|---|---|
| 3,772,485 A | 11/1973 | Workings | |
| 4,163,879 A | 8/1979 | Mayer et al. | |
| 4,292,969 A * | 10/1981 | Raible | A61M 39/28 251/340 |
| 5,014,750 A * | 5/1991 | Winchell | A61M 5/141 138/42 |
| 5,113,904 A | 5/1992 | Aslanian | |
| 5,938,642 A * | 8/1999 | Burroughs | A61M 5/31551 604/208 |
| 6,001,089 A * | 12/1999 | Burroughs | A61M 5/31551 604/208 |
| 6,183,441 B1 * | 2/2001 | Kriesel | A61M 5/152 604/132 |
| 6,916,010 B2 | 7/2005 | Beck et al. | |
| 7,220,245 B2 * | 5/2007 | Kriesel | A61M 5/14244 604/134 |
| 7,361,165 B2 * | 4/2008 | Simon | A61M 5/16804 604/246 |
| 7,695,454 B2 * | 4/2010 | Barron | A61M 5/31541 604/187 |
| 8,362,382 B2 * | 1/2013 | Koizumi | H01H 19/003 200/11 TW |
| 8,544,815 B2 | 10/2013 | Avery et al. | |
| 2003/0135164 A1 * | 7/2003 | Simon | A61M 5/16804 604/246 |
| 2004/0054326 A1 | 3/2004 | Hommann et al. | |
| 2007/0083176 A1 * | 4/2007 | Voege | A61M 39/22 604/378 |
| 2008/0154216 A1 | 6/2008 | Simon | |
| 2010/0198154 A1 * | 8/2010 | Simon | A61M 5/14 604/118 |
| 2010/0229857 A1 * | 9/2010 | Von Schuckmann | A61M 15/009 128/200.23 |
| 2011/0015580 A1 * | 1/2011 | Stroup | A61M 5/16881 604/207 |
| 2012/0245515 A1 * | 9/2012 | Calasso | A61M 5/1413 604/67 |
| 2013/0158468 A1 * | 6/2013 | Bernstein | A61B 5/150022 604/27 |

FOREIGN PATENT DOCUMENTS

| | | |
|---|---|---|
| DE | 10195354 T1 | 5/2003 |
| EP | 295075 A1 | 12/1988 |
| EP | 730876 A2 | 9/1996 |
| EP | 1415675 A1 | 5/2004 |
| GB | 462057 A | 3/1937 |
| JP | 2002503116 A | 1/2002 |
| JP | 2005515032 A | 5/2005 |
| JP | 2008206572 A | 8/2008 |
| JP | 2010512941 A | 4/2010 |
| WO | WO-8600682 A1 | 1/1986 |
| WO | 9627400 A1 | 9/1996 |

OTHER PUBLICATIONS

Notification of Reasons for Rejection for Japanese Application No. 2016-522450, dated Jan. 23, 2018 with translation, 7 pages.
Chinese Office Action for Chinese Application No. 201480034701.5, dated May 3, 2018, with English translation, 10 pages.
Notification of Reasons for Rejection for Japanese Application No. 2016-522450, dated Oct. 2, 2018, with translation, 8 pages.

* cited by examiner

ADJUSTING DEVICE FOR A FLOW CONTROLLER

CROSS-REFERENCE TO RELATED APPLICATIONS

This application is a national stage application under 35 U.S.C. § 371 of PCT Application No. PCT/EP2014/063312, filed on Jun. 24, 2014, which claims priority to and the benefit of German Application No. 102013212325.6 filed on Jun. 26, 2013, which are incorporated herein by reference in their entirety.

The present invention relates to an adjusting device for adjusting the flow rate of a medical fluid conveying system.

A medical fluid conveying system can be e.g. an infusion device for infusion therapy or for infusion of an analgesic into a patient. When using such fluid conveying systems, it is necessary to select and set one among a plurality of possible flow rates for the conveyance of the fluid. Adjusting the fluid rate for fluid conveyance must be performed with high precision and reliability. Particularly in infusion devices, a wrong setting may cause an over- or underdosage with potentially critical consequences for the patient.

It is known to perform the adjusting of the flow rate with the aid of a rotary control device. In this case, a selection wheel is provided for selecting one of a plurality of possible flow rates. An adjusting disk for adjusting the selected flow rate is fixedly connected to said selection wheel for common rotation therewith. In this arrangement, the radially outer edge of said adjusting disk cooperates with a detent. The engagement between the detent and the adjusting disk is provided in such a manner that the detent will lock the adjusting disk, and thus also the selection wheel, in the respective rotary position required for adjusting the desired flow rate.

A problem in known adjusting devices resides in that the device may happen to be set to an intermediate point between adjacent adjustment positions for respective flow rates, where neither the one nor the other one of these flow rates will have been selected. In case of such an occurrence, the erroneously set intermediate position will remain set further on. Depending on the regulating mechanism, this can lead to a maximum conveyance or to non-conveyance of the fluid. Primarily in medical treatment performed by infusion, this can entail critical consequences for a patient.

It is an object of the invention to provide an improved adjusting device for adjusting the flow rate of a medical fluid conveying system.

The adjusting device according to the invention is defined by the features defined in claim 1. Thus, the adjusting disk is star-shaped. The star-shaped design is lending the adjusting disk a rotationally symmetrical shape comprising a radially outer edge having a plurality of regions with maximum radius and a plurality of regions with minimum radius. The regions where said radially outer edge has the maximum radius can be referred to as peaks, and the regions with minimum radius can be referred to as valleys. As a result of the star-shape of the adjusting disk, the valleys and the peaks alternate with each other. The cooperation of the detent and the star shape of the adjusting disk will result in a stable position of the adjusting disk if the detent engages a valley, and in an instable position if the detent engages a peak. In this regard, it is decisive that a peak does not have a constant radius but a maximum radius which decreases toward the adjacent valley. Thereby, engagement of the detent on a peak will result in an instable rotary position of the adjusting disk. While the valleys serve to attain the rotary positions for adjusting a respective flow rate, the intermediate peaks correspond to rotary points between mutually adjacent rotary positions of settable flow rates. Thus, erroneously setting a rotary position between adjacent flow rates will cause an instable rotary position of the adjusting disk.

A detent which is supported against the force of a spring and is urged by said spring against the radially outer edge of the adjusting disk, will have the effect, when abutting on the radially outer edge at a site between adjacent valleys, that the spring force will cause the adjusting disk to rotate out of its instable position, thus moving the detent into a valley and, therefore, into a stable position. In this arrangement, the detent can be formed as a projection on a bending spring, e.g. as a triangular projection with a pointed tip. By way of alternative, the detent can also be formed as a spike connected to a spring, e.g. to a spiral spring.

The star shape of the adjusting disk preferably results in a zigzag shape of said radially outer edge, wherein adjacent lines of this zigzag shape are inclined relative to each other at an angle in the range from 10° to 155° and preferably in the range from 90° to 135°.

An exemplary embodiment of the invention will be explained in greater detail hereunder with reference to the accompanying Figures in which FIG. 1 is a view of the adjusting device as seen from the direction of the rotary axis;

Figure 4:
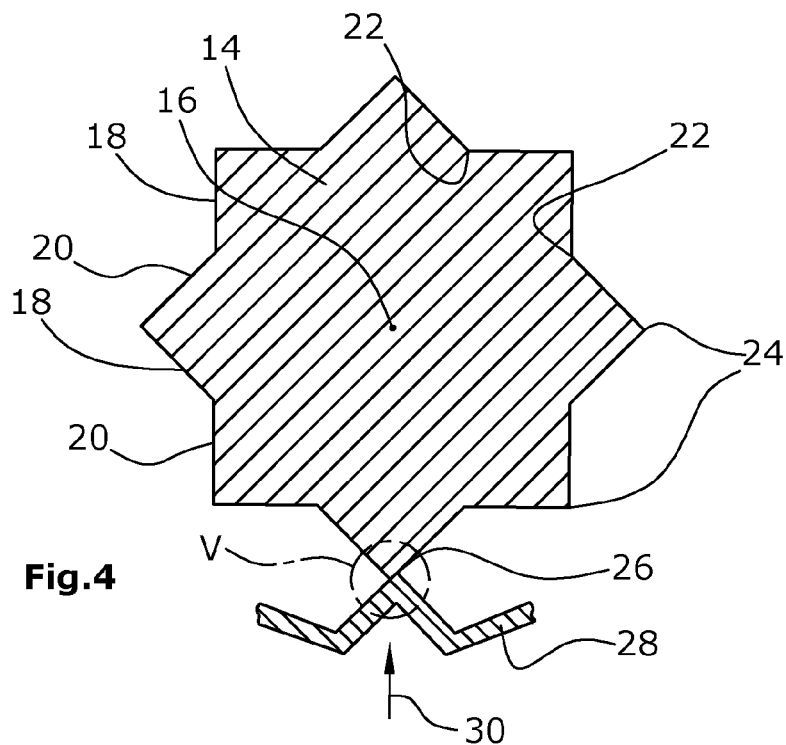
FIG. 4 is a sectional view similar to FIG. 3, in a second rotary position.
Figure 5:
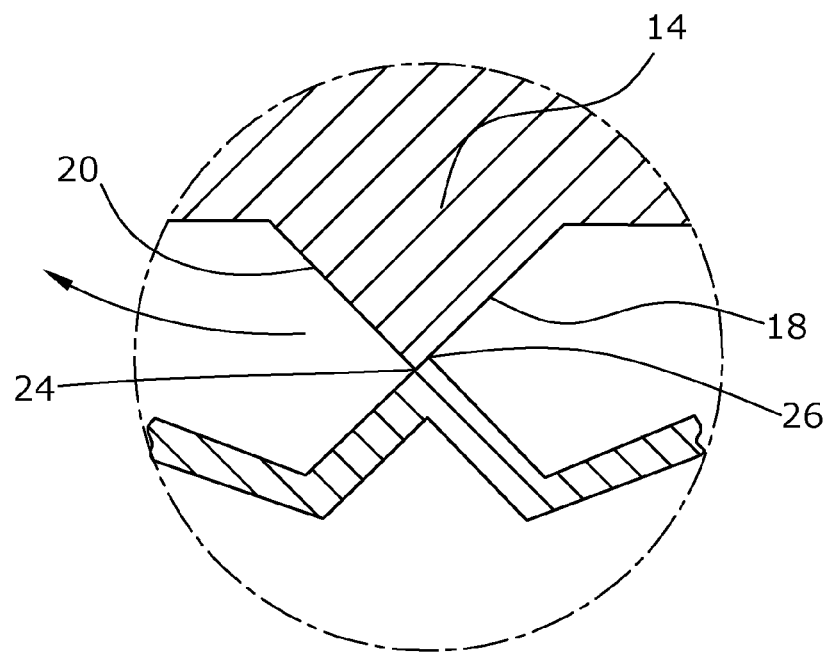

FIG. 5 the detail marked by V in FIG. 4.

Figure 1:
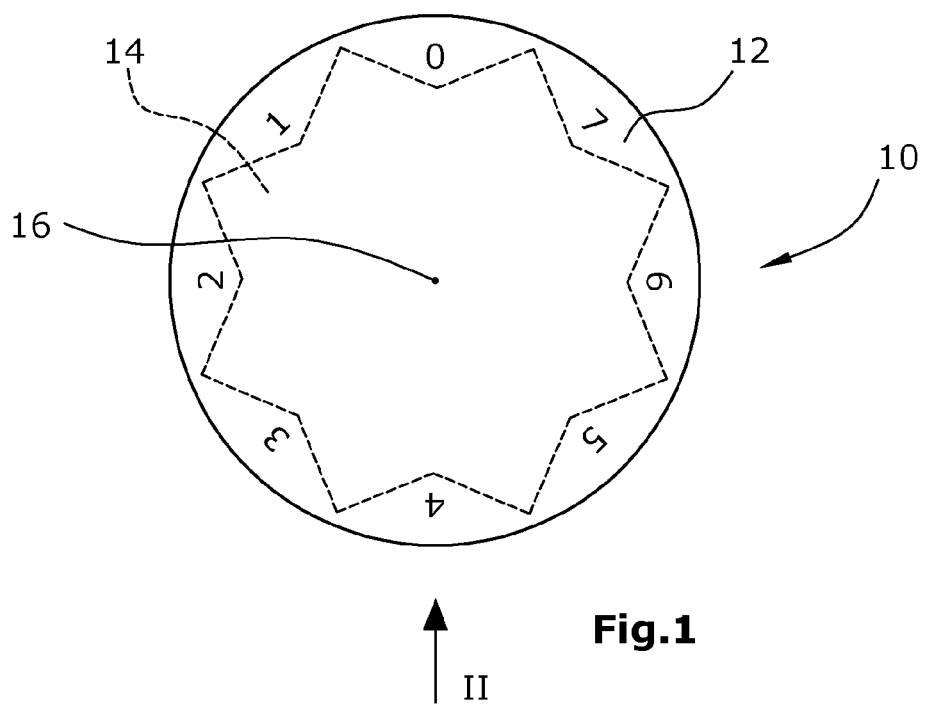
Figure 2:
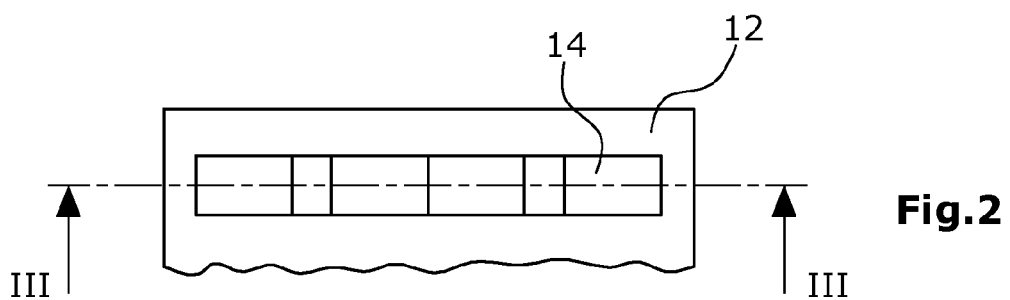
FIG. 2 is a view from the direction indicated by arrow II in FIG. 1.

FIG. 1 is a view of the adjusting device 10, with the surface of the selection wheel 12 being shown as viewed from the rotational axis of the wheel. Along the radially outer edge of selection wheel 12, digits 0-7 are represented at regular mutual intervals for marking the rotary positions corresponding to said digits. Each of the digits 0-7 is assigned to a possible settable flow rate, wherein 0 corresponds to the absence of a flow and 7 corresponds to maximum flow.

Selection wheel 12 is of a circular shape as shown in FIG. 1 and is supported for rotation around a rotary axis 16. Selection wheel 12 is tightly connected to a rotationally symmetrical adjusting disk 14 so that the adjusting disk 14 can rotate about the same rotary axis 16. Selection wheel 12 and adjusting disk 14 are fixedly coupled to each other for common rotation. In FIG. 1, adjusting disk 14 is schematically indicated as a covered element behind selection wheel 12.

Adjusting disk 14 has a star-shaped contour formed by zigzag lines 18, 20 along its outer periphery. The star shape can be seen in the viewing direction along rotary axis 16, as shown in FIGS. 3 and 4.

Said zigzag lines 18, 20 of the radially outer edge of adjusting disk 14 are straight lines and are arranged relative to each other at flat angles in a range from about 110° to about 130°. At their contact points, adjacent zigzag lines 18, 20 form valleys 22 and peaks 24. In this configuration, each peak 24, shaped as a radially outward tip, forms a point with maximum radius. In a corresponding manner, each valley 22, shaped as a radially inward tip, forms a point with minimum radius. The radii of all valleys 22 are identical with each other, and also the radii of all peaks 24 are identical with each other.

Figure 3:
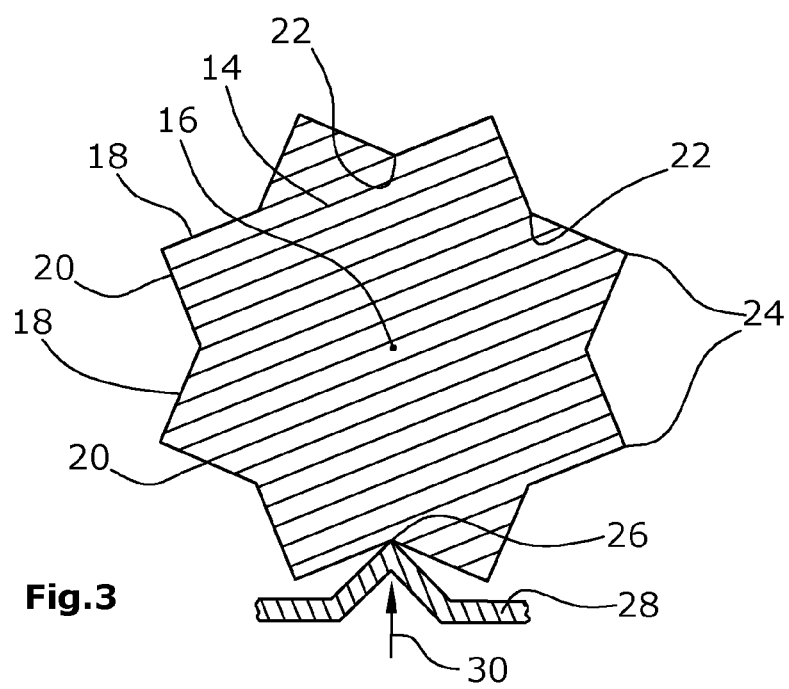
FIG. 3 is a sectional view taken along line in FIG. 2, in a first rotary position.

The zigzag lines 18, 20 of the star-shaped radially outer edge of adjusting disk 14 are engaged by a detent 26 which, as illustrated in FIGS. 3-5, is formed as a triangular tip of a bending spring 28. In the present exemplary embodiment, said bending spring 28 is a bent leaf spring. In relation to adjusting disk 14, bending spring 28 is arranged in a manner causing the spring force to urge the detent 26—in the direction shown by arrow 30 in FIGS. 3 and 4—radially inward against adjusting disk 14.

FIG. 3 shows the stable position of adjusting disk 14, with spring 28 pressing detent 26 into a valley 22 of the star shape. When the adjusting disk 14 is to be rotated by turning the selection wheel 12, there has to be applied a force which counteracts the force that the bending spring 28 exerts via detent 26 onto the outer edge of adjusting disk 14. In case of inadvertent adjustment of an intermediate position between adjacent valleys, the adjusting disk 14 will always be placed into an instable state. An example of an intermediate position is shown in FIGS. 4 and 5. In such a situation, the star shape has the effect that the detent 26, under the influence of the force of bending spring 28, will press obliquely against the edge of adjusting disk 14, thus causing the adjusting disk 14 to rotate until the detent 26 will come to rest in one of the valleys. In this manner, setting an intermediate position between adjacent valleys is prevented.

The invention claimed is:

1. An adjusting device for adjusting a flow rate of a medical fluid conveying system, said adjusting device comprising a selection wheel for selecting one of a plurality of flow rates, an adjusting disk connected to the selection wheel and provided for adjusting the flow rate, and a detent comprising a pointed tip in engagement with an outer edge of the adjusting disk,
   wherein said adjusting disk has a star shape comprising a plurality of peaks and valleys along the outer edge of the adjusting disk, each valley comprising a point of minimum radius, and
   wherein the adjusting disk is rotatable between a plurality of stable positions, in which the pointed tip engages the outer edge of the adjusting disk at a point of minimum radius in one of the valleys, and a plurality of unstable positions, in which the pointed tip presses obliquely against the outer edge of the adjusting disk to urge the adjusting disk to one of the plurality of stable positions, so as to prevent the adjusting disk from remaining in an intermediate position between adjacent valleys,
   wherein the detent defines a first detent edge and a second detent edge that intersects the first detent edge at the pointed tip, the first detent edge separated from the second detent edge by a first angle,
   wherein each valley defines a first valley edge and a second valley edge that intersects the first valley edge at one of the points of minimum radius, the first valley edge separated from the second valley edge by a second angle, and
   wherein the first angle of the pointed tip is smaller than the second angle of each valley such that the pointed tip directly contacts each and every point of minimum radius when the adjusting disk is rotated.

2. The adjusting device according to claim 1, wherein said star shape forms a zigzag shape of the outer edge of the adjusting disk.

3. The adjusting device according to claim 1, wherein each of said valleys corresponds to a rotary position of the selection wheel and the adjusting disk as required for adjusting a respective flow rate.

4. The adjusting device according to claim 1, wherein each of said peaks corresponds to a rotary position of the selection wheel and the adjusting disk which is situated exactly between two mutually adjacent rotary positions for corresponding flow rates.

5. The adjusting device according to claim 2, wherein adjacent lines of the zigzag shape are arranged relative to each other at an angle in a range from 10° to 155°.

6. The adjusting device according to claim 1, wherein the peaks and/or the valleys are respectively rounded.

7. The adjusting device according to claim 1, wherein said detent is supported against a force of a spring in such a manner that an engagement of the detent within a valley positions the adjusting disk in one of the stable positions, and an engagement of the detent with a peak positions the adjusting disk in one of the unstable positions.

8. The adjusting device according to claim 1, wherein the detent is formed as a projection on a bending spring.

9. The adjusting device according to claim 1, wherein the detent is formed as a spike connected to a spring.

10. The adjusting device according to claim 3, wherein each of said peaks corresponds to a rotary position of the selection wheel and the adjusting disk which is situated exactly between two mutually adjacent rotary positions for corresponding flow rates.

11. The adjusting device according to claim 7, wherein the spring biases the detent inwardly against the adjusting disk in the stable and unstable positions.

12. The adjusting device according to claim 1, wherein the pointed tip presses obliquely against the outer edge of the adjusting disk in the unstable positions to cause the disk to rotate until the detent comes to a rest in one of the plurality of valleys.

13. An adjusting device for adjusting a flow rate of a medical fluid conveying system, said adjusting device comprising a selection wheel for selecting one of a plurality of flow rates, an adjusting disk connected to the selection wheel and provided for adjusting the flow rate, and a detent comprising a pointed tip in engagement with an outer edge of the adjusting disk,
   wherein said adjusting disk has a star shape comprising a plurality of peaks and valleys along the outer edge of the adjusting disk, each valley comprising a point of minimum radius, and
   wherein the adjusting disk is rotatable between a plurality of stable positions, in which the pointed tip engages the outer edge of the adjusting disk at a point of minimum radius in one of the valleys, and a plurality of unstable positions, in which the pointed tip presses obliquely against the outer edge of the adjusting disk to urge the adjusting disk to one of the plurality of stable positions, so as to prevent the adjusting disk from remaining in an intermediate position between adjacent valleys, and
   wherein the pointed tip of the detent is maintained in constant engagement with the outer edge of the adjusting disk at all times by a spring, such that the pointed tip is always in contact with the outer edge during rotation of the adjusting disk.

* * * * *